June 16, 1953 C. D. CORLISS Plant Pat. 1,194
EUONYMUS FORTUNEI PLANT
Filed Jan. 5, 1951
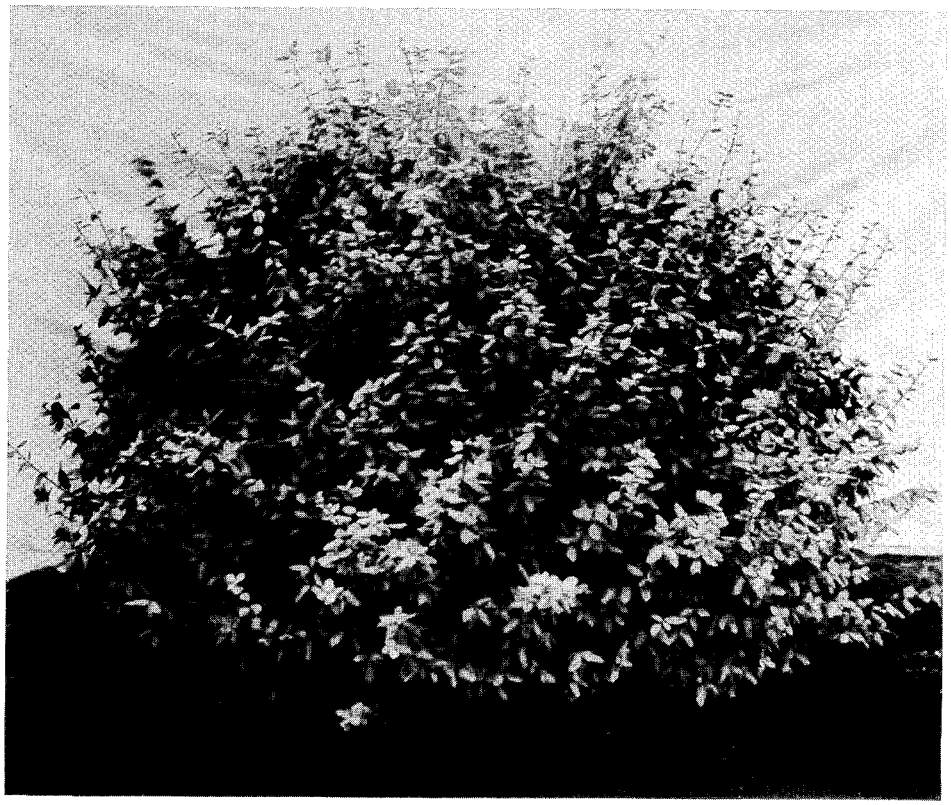
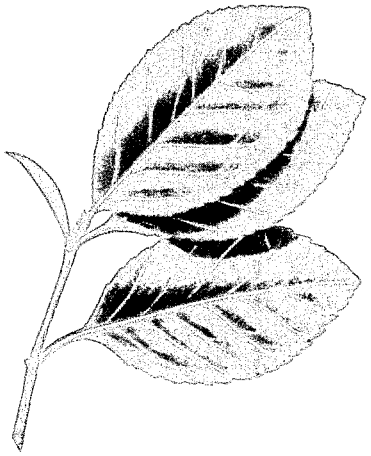
INVENTOR
Clifford D. Corliss
By Orville M. Kile
Plant Patent Agt.

Patented June 16, 1953

Plant Pat. 1,194

UNITED STATES PATENT OFFICE 1,194

EUONYMUS FORTUNEI PLANT

Clifford D. Corliss, Gloucester, Mass., assignor to Corliss Bros., Inc., Gloucester, Mass., a corporation of Massachusetts Application January 5, 1951, Serial No. 204,519

1 Claim. (Cl. 47—59)

My present invention relates to a new and distinct variety of evergreen Euonymus plant originating as the result of crosses made by me between *Euonymus fortunei vegeta* and *fortunei carrierei* for a number of years in an effort to obtain a sturdy, vigorous, upright but low-growing, broad-leaved shrub of decorative value. It is a striking variation from parental type and possesses definite decorative value not found in either parent.

This new variety has been reproduced by means of cuttings at nurseries located at Gloucester, Massachusetts. The only means of reproduction of this plant is asexual and young plants thus obtained exhibit the same characteristics as the original selected plant.

The habit of growth of my new variety answers a long-recognized want for a hardy broadleaved evergreen of the semi-dwarf type, suitable for landscape foundation plantings of homes, buildings and corners, and as an additional specimen shrub.

Unlike either parent, this variety is a well-shaped, distinct shrub, with branches growing laterally from a central trunk and gracefully ascending without support.

Outstanding among its features is its adaptability to various growing conditions. It will grow well in either full sun or semi-shade, is not particular as to soil requirements, and grows satisfactorily in either dry or very moist locations. The original plant has been exposed to extremely low temperatures (much below zero) over a number of years without any indication of injury, and severe droughts to which it has been subjected have not affected it adversely.

The distinctive characteristics of my new variety will be more clearly apparent by referring to the accompanying illustration and to the detailed description which follows. The illustration shows a black-and-white photograph of the original plant of this new variety, indicating particularly the type of growth and symmetrical shape of the unsupported plant. Also in the lower left-hand corner is shown a twig of this variety with leaves and stem in approximately true colors. Color designations in the detailed description refer to the usual dictionary meaning, except that where plate numbers are used, Ridgway's Color Standards and Nomenclature is indicated.

Growth:

*Habit.*—Sturdy and vigorous.

*Form.*—Compact and shrubby; broader than tall, original specimen having attained a height of 5 feet and a spread of 6 to 7 feet. It is well filled out at the base clear to the ground, with branches growing laterally from a central trunk and ascending in graceful curves.

Leaves:

*Type.*—Evergreen; petioled.

*Quantity.*—Abundant.

*Position.*—Opposite.

*Shape.*—Elliptical to elliptic-ovate. Apex acute. Base acute. Margin finely crenate and reflexed.

*Color.*—Lustrous dark green above, between Cress Green (Pl. XXXI) and Cedar Green (Pl. VI), with slightly lighter colored veins. Light green beneath, approximately Parrot Green (Pl. VI).

*Size.*—Medium. Somewhat smaller than leaves of *carrierei* which they otherwise resemble. Largest are about 2 inches long and 1⅛ inches wide.

*Texture.*—Leathery.

*Petiole.*—Approximately ¼ inch long.

Branchlets: Medium green; minutely warty.

Internodes: Approximately 1¼ inches long.

Buds: Narrow; long-pointed.

Bud scales: Imbricated.

Roots: Strong and fibrous, permitting transplanting without difficulty.

Hardiness: Exposure to below zero temperatures for a number of years has shown no indication of injury.

Drought tolerance: Severe drought conditions have had no adverse effect.

Flower: Inconspicuous; borne in axillary cymes.

Fruit:

*Shape.*—Sub-globose; lobed; usually warty capsule.

*Borne.*—In solitary capsule on axially pedicel.

*Quantity.*—This variety fruits sparingly, as contrasted with the freely-produced fruits of the parent *carrierei*.

*Color.*—More reddish-purple than that produced by *vegetus* parent.

*Seed.*—Borne 1 to 4 in each capsule. White, each seed being covered with bright orange aril.

Having thus disclosed my invention, I claim:

The new and distinct variety of broadleaf evergreen Euonymus plant, substantially as herein shown and described, characterized particularly by its adaptability to landscape and specimen planting and to various soil, sun and temperature conditions; its extreme hardiness and drought tolerance; its habit of upright growth from a central trunk, with branches growing laterally and gracefully ascending without support into a well-rounded, dense shrub which is broader than tall and well bushed down to the ground; its strong fibrous roots which assure ease of transplantation; its medium-sized, elliptical, dark green leaves; its narrow, long-pointed leaf buds; and the reddish-purple color of its seed capsule.

CLIFFORD D. CORLISS.

No references cited.